United States Patent [19]

McGill et al.

[11] 4,386,209

[45] May 31, 1983

[54] CHICHIBABIN REACTION

[75] Inventors: Charles K. McGill, Indianapolis; James J. Sutor, Greenwood, both of Ind.

[73] Assignee: Reilly Tar & Chemical Corporation, Indianapolis, Ind.

[21] Appl. No.: 366,598

[22] Filed: Apr. 8, 1982

[51] Int. Cl.³ .......................................... C07D 213/73
[52] U.S. Cl. ................................... 546/311; 546/297; 546/304; 546/309; 546/310
[58] Field of Search ............... 546/311, 304, 309, 310, 546/297

[56] References Cited

PUBLICATIONS

Chichibabin et al., "J. Russ. Phys. Chem. Soc.", vol. 46, pp. 1216-1236 (1914).
Novikov et al., "Khim. Get. Soedin".
Abramovitch et al., "Chem. and Industry", (1964) pp. 659-660.
Abramovitch et al., "Can. J. Chem.", vol. 43, No. 4, pp. 725-731 (1965).
Abramovitch, "Advances in Heterocyclic Chem.", vol. 6, pp. 294-295 (1966).
Vadja et al., "Reg. Trav. Chim.", vol. 80, pp. 47-54 (1961).

*Primary Examiner*—Robert T. Bond
*Attorney, Agent, or Firm*—Woodard, Weikart, Emhardt & Naughton

[57] ABSTRACT

In a Chichibabin amination of a pyridine base by sodamide in an organic solvent, the improvement comprising conducting the reaction under pressure of at least about 50 psi in the gas phase above the reaction mixture and adding ammonia to the mixture sufficient to produce a partial pressure of ammonia of at least about 5 psi in the gas phase. Preferred temperature and pressure ranges are disclosed, as are catalysts and other preferred steps for practicing the reaction. Significant results are obtained including improved and changed yields from those classically expected in Chichibabin aminations, including new compositions of matter in at least one case.

47 Claims, No Drawings

CHICHIBABIN REACTION

BACKGROUND OF THE INVENTION

This invention relates generally to amination of nitrogen-containing heterocycles by alkali metal amides, and in particular to a significant discovery with respect to the time-honored Chichibabin amination reaction.

In 1914, Chichibabin and Seide first reported that -picoline, or more commonly 2-methypyridine, underwent direct amination in the free-position on the ring when treated with sodium amide in toluene at elevated temperatures. Chichibabin and Seide, *J. Russ. Phys. Chem. Soc.*, 46, 1216 (1914). This reaction was later extended by Chichibabin and his contemporaries to amination of many pyridine, quinoline and isoquinoline bases. It has since been recognized as one of the more important and influential developments in pyridine chemistry, so much so that the reaction itself has become synonymous with the name of its discoverer. Its commercial importance should also not be discounted as, for example, the 2-amino amination product of pyridine itself has become an enormously important and useful starting material for further synthesis in many areas.

The Chichibabin reaction has been the subject of much study and comment through the years, both as to scope and as to the mechanism of the amination. For example, although first carried out in toluene, the reaction has since been carried out in other aprotic solvents of which dialkylanilines, liquid paraffin and other hydrocarbons such as benzene, xylene, cumene, mesitylene and petroleum fractions are most common. Similarly, although first accomplished using sodium amide, or more commonly sodamide, the reaction has since been carried out with other metal amides such as potassium amide, barium amide, etc., particularly when using low temperatures and long reaction times in attempting to slow the reaction to study the mechanism of this amination process. The Chichibabin mechanism remains one of the least understood nucleophilic substitution reactions in heterocyclic chemistry owing to the difficulty in handling the alkali metal amides and in studying kinetics of a process which takes place under heterogeneous conditions at high temperatures. Classicly, those conditions have included heating the mixture at atmospheric pressure and at temperatures between about 100°–200° C. Another characteristic feature has been the evolution of hydrogen gas and ammonia gas which signals the start of the reaction and identifies its progress toward completion. Novikov, Pozharskii & Doron'kin, Translated from *Khim. Geterotsikl. Soedin.*, No. 2, 244 (1976); Levitt & Levitt, *Chem. & Ind.*, 1621 (1963).

The base compound which undergoes amination has also received much study. Reports document the amination of mono and diazines such as pyridines, quinolines, isoquinolines, benzoquinolines, phenanthridines, acridines, benzimidazoles, quinazolines, naphthyridines, pyrimidines, pyrazines and other heterocyclic systems. Reactions related to the Chichibabin amination have also been studied which are not heterocycles, but have a N=CH group such as Schiff bases. Pozharskii, Simonov and Doron'kin, *Russ. Chem. Rev.*, 47, 1042 (1978), Translated from *Uspekhi Khim.*, 47, 1933 (1978). The result of these efforts is that the predictability of Chichibabin aminations is thought to be high for a given base compound, as are the expected product or products of the reaction. Although such certainty is helpful, situations arise where a partial or complete change in the Chichibabin result is desirable. For example, expected products may not be desired, or new products may be wanted, or isomer ratios may be preferably reversed.

An important example of this last category is the case of 3-substituted pyridine bases, and particularly 3-alkyl derivatives, which are known to undergo Chichibabin amination to produce predominantly 2-amino-3-alkylpyridine ("2,3-isomer") and to a much lesser extent 2-amino-5-alkylpyridine ("2,5-isomer"). The amination of 3-methylpyridine, also known as 3- or β-picoline, is an excellent example, which reportedly yields the 2,3- and 2,5-isomers in a ratio of about 10.5:1. Abramovitch, *Advan. Heterocycl. Chem.*, 6, 294 (1966); Abramovitch, Helmer and Saha, *Chem. & Ind.*, 659 (1964); Abramovitch, Helmer and Saha, *Can. J. Chem.*, 43, 727 (1965). This is highly unfortunate as the 2,5-isomers are much preferred because of their usefulness as starting materials and intermediates for the preparation of herbicides, insecticides and pharmaceuticals. Chemical manufactures are hard-pressed to meet the demand for 2,5-products since they are left with very large quantities of largely unusable 2,3-isomer at this time. Understandably, there is thus a substantial need to change the classic Chichibabin amination in this case in a way that improves the yield of these 2,5-products, of which 2-amino-5-methylpyridine is most preferred, at least at this time.

Notwithstanding the many years of study of the Chichibabin reaction, no significant breakthrough has been reported which teaches or suggests a methodology to change the reaction's classic mechanism or its anticipated results given a particular heterocyclic base compound. That is, not until now.

SUMMARY OF THE INVENTION

Applicants' invention does just that, and in so doing, addresses much more than the specific need for improving preparation of these 2,5-isomer products. Applicants have discovered a major improvement to the classic Chichibabin amination involving conducting the reaction under pressure in the gas phase above the solid liquid heterogeneous reaction mixture and having a partial pressure of ammonia in the gas phase at least equal to the autogenous pressure of ammonia generated in situ by the reaction.

In its preferred forms, applicants' work thus far improves the classic Chichibabin amination of a pyridine base by sodamide in an organic solvent, by pressurizing the reaction vessel to an initial pressure of at least about 50 pounds per square inch (psi) coupled with adding ammonia to the vessel sufficient to produce an initial partial pressure of ammonia of at least about 5 psi in the gas phase. Characteristics of other alternate forms include conducting the reaction in a substantially inert atmosphere at temperatures between about 100°–250° C. and without refluxing the mixture as is common in the classic Chichibabin reaction. The added ammonia may be injected in gaseous form, or left as liquid ammonia in the reaction mixture as when sodamide is prepared in situ by reacting sodium in excess liquid ammonia prior to conducting the amination. The temperature and pressure in the vessel are preferably maintained for a period sufficient to cause substantial amination to occur as measured by the production of hydrogen gas by the reaction, although both may vary from their initial settings. For example, temperature is preferably maintained between about 130°–200° C. whereas reaction pressures of at least about 300 psi are preferred with at least about 15–50 psi of ammonia being initially present. The autogenous pressure of gases evolved during amination can be used to pressurize the reaction vessel, and excess gases can be vented off to prevent too much build up.

Applicants have also discovered that a beneficial effect is achieved by adding a catalyst to the reaction, preferably an aminopyridine and more preferably one or more of the desired products of the reaction. And in yet another alternate method of characterizing applicants' preferred invention, it is the improvement of increasing pressure and adding ammonia to the gas phase above the reaction mixture sufficient to increase yield by at least about one third of a product expected in the Chichibabin amination or to produce a yield of at least about 10% of a product not expected in the Chichibabin amination, each yield being as a percent of total amination products obtained.

The specific products of applicants' work have varied with the pyridine base used and the conditions observed. Applicants have discovered, however, that results at least as good as those classically expected have been achieved and that for most bases tested to date, a significant change was observed in the product or products expected to result from a Chichibabin amination. As to whether anticipated products increase or decrease in yield, or new ones appear, or isomer ratios vary, reference should be made to the specific examples which follow. In the case of at least one base, new compositions of matter were obtained.

Further objects and advantages of the present invention will become apparent from the description of the preferred embodiments which follows.

DESCRIPTION OF THE PREFERRED EMBODIMENTS

For the purposes of promoting an understanding of the principles of the invention, reference will now be made to the several embodiments of applicants' work and specific language will be used to describe the same. It will nevertheless be understood that no limitation of the scope of the invention is thereby intended, such alterations and further modifications, and such further applications of the principles of the invention therein being contemplated as would normally occur to one skilled in the art to which the invention relates.

In its broadened form, one embodiment of applicants' invention was the discovery that significant and in most cases surprising results were achieved by conducting a Chichibabin amination of a pyridine base by sodamide in an organic solvent under pressure with some addition of ammonia to produce a partial pressure of ammonia in the gas phase above the solid liquid heterogeneous reaction mixture. Specific results varied with the base used, as shown in the examples which follow. It can be said, however, that the results were at least as good as classically expected in all cases and that with all but a few bases tested thus far, the results differed significantly from anticipated products and percentages of classic Chichibabin aminations.

In a preferred form, after the reactants were combined in a pressure vessel the gas phase above the mixture was initially pressurized to at least about 50 psi and ammonia was added to the vessel sufficient to produce an initial partial pressure of ammonia of at least about 5 psi in this gas phase. The mixture was brought to a temperature sufficient to cause amination to occur, and pressure was maintained at or above this initial 50 psi level during the course of the reaction until hydrogen evolution had substantially ceased. Although the autogenous pressure of gases evolved in situ during amination was used to assist in maintaining pressure during the reaction, it was preferred to initially purge the vessel of air and pressurize it using an inert gas such as nitrogen and then to conduct the amination in the substantially inert nitrogen atmosphere. In this regard, the term "substantially" is meant to define the condition that develops during amination in which evolved hydrogen and possible other gases enter the gas phase resulting in a predominent, but not totally inert nitrogen atmosphere.

It was more preferred in this embodiment to have an initial ammonia pressure of at least about 15–50 psi in the gas phase. Most preferred at this time was about 45 psi. As the amination proceeded, it was found that some ammonia was lost in venting off excess pressure due to hydrogen and other gases being evolved without detracting from the results of the reaction. This depends, of course, upon the size and efficiency of the pressure vessel and condenser used.

In another method of characterizing an alternate preferred form of applicants' invention, it was the improvement of a classic Chichibabin amination comprising increasing pressure and adding ammonia to the gas phase above the reaction mixture sufficient to increase yield by at least about one third of a product expected in the Chichibabin amination or to produce a yield of at least about 10% of a product not expected in the Chichibabin amination, each yield being as a percent of total amination products obtained. The specific products of applicants' work have varied with the pyridine base used and the conditions observed. In the case of at least one base, namely 3-(3-phenylpropyl)pyridine, new compositions of matter were obtained. For more detail as to the specific products obtained thus far, reference should be made to the specific examples which follow.

Several sources of ammonia were used. For example, in one embodiment sodamide was prepared in situ by reacting sodium in excess liquid ammonia. After the sodamide was prepared, some of the liquid ammonia was removed and an organic solvent was added to the same vessel. The pyridine base was combined in the vessel. Enough liquid ammonia remained so that when the mixture was brought to a temperature sufficiently high to cause amination to begin, the partial pressure of the remaining ammonia in the gas phase was sufficient to achieve the beneficial effect of the invention. In similar fashion, quantities of liquid ammonia or compounds which disassociate into free ammonia are usable to provide the ammonia source. Most preferred, however, was direct injection of gaseous ammonia into the vessel during pressurizing of the gas phase.

As to other conditions of the reaction, after bringing the mixture to a temperature sufficiently high to cause hydrogen evolution (and thus amination) to begin, the reaction mixture was maintained at a temperature sufficiently high to cause, or to permit, substantial amination to take place. A temperature range of between about 100°–250° C. was preferred, while most preferred was a range of about 130°–200° C. based on experiments to date. The length of time required for amination depended, of course, upon many variables and has no importance or distinction with regard to the invention.

Experimental times varied between about 5–20 hours to arrive at commercially practical yields. As to the solvent used, toluene and xylene were preferred although other organic solvents work equally well. Many such solvents are common to Chichibabin aminations.

Applicants' work to date has concentrated on amination of pyridine bases using their improved Chichibabin procedure. In this regard, the term "pyridine base" is understood to include pyridine itself and all substituted pyridines or pyridine derivatives. Of those tested thus far, the yields from pyridine and 2-aminopyridine were comparable to or slightly better than would be expected in classic Chichibabin aminations of these bases. Tests of 3- and 4-aminopyridine have not given significant yields of diaminopyridines either under classic conditions or under applicants' invention. Other bases tested have shown surprising and unexpected results, differing greatly from their classic reactions as pointed out in detail in the specific examples which follow. Those tested include pyridine; aminopyridines including 2-aminopyridine, 3-aminopyridine and 4-aminopyridine; 3-picoline; nicotinic acid; nicotinamide; 3-hydroxypyridine; 4-dimethylaminopyridine; 4-(5-nonyl)pyridine; 3-lower alkylpyridines including 3-ethylpyridine, 3-propylpyridine, 3-isopropylpyridine and 3-butylpyridine; 3-(3-phenylpropyl)pyridine; 3-phenylpyridine; and 3,4-lutidine.

The most preferred embodiment to date in applicants' work has comprised the step of adding an amount of pyridine base to a pressure vessel such as an autoclave in which sodamide has been preformed in at least a slight stoichiometric excess. This adding step took place at room temperature and with the prior addition of an organic solvent such as toluene or xylene and possibly a dispersing agent such as oleic acid. The vessel was then sealed, purged of air with nitrogen, and pressurized to about 45 psi with gaseous ammonia and to about 200 psi with nitrogen in the gas phase above the solid liquid heterogenous reaction mixture. The vessel and its contents were heated rapidly with stirring to between about 130°–200° C. at which time evolution of hydrogen gas began, thereby signaling the start of amination. The pressure in the vessel increased because of this temperature rise and because of gas evolution even without further pressurizing with nitrogen gas. The temperature was maintaned at or somewhat below this 130°–200° C. range and the pressure was maintained between about 300–1000 psi as a commercially practicable range, with about 350 psi being most preferred, for a period of about 5 hours or until hydrogen evolution had substantially ceased. Excess pressure was vented off during the reaction through a pressure relief valve or other means. At the end of the amination, the vessel was allowed to cool to room temperature and was vented to atmospheric pressure. The reaction mixture was hydrolyzed and removed, and the products of the reaction were isolated using standard procedures.

In an alternate embodiment of this most preferred procedure, a catalyst was also added to the mixture prior to pressurizing the vessel to help initiate the reaction and encourage formation of the desired product or products. Applicants have found aminopyridine compounds to be preferred catalysts for this purpose, although most preferred has been the use of one or more of the desired products of the particular reaction. In the amination of 3-picoline, for example, the catalyst of choice was a mixture of various ratios of the 2,5- and 2,3-isomer products.

In an effort to further describe and define in detail the nature and scope of the invention, the following specific examples are now given of improved Chichibabin aminations which have been performed using applicants' discovery. In these examples as in the entire specification and the claims which follow, temperatures are given in degrees centigrade (°C.) and pressures are given in pounds per square inch absolute (psi) unless otherwise stated.

EXAMPLE 1

Amination of 3-Picoline

In a liter, 3 neck flask, equipped with a mechanical stirrer, was prepared 1.3 moles of sodamide by slowly adding 29.9 g of sodium to about 700 cc of liquid ammonia containing a catalytic amount of ferric nitrate hexahydrate. The ammonia was substantially evaporated and replaced with 300 cc of xylene containing 0.1 cc of oleic acid. At room temperature, 93 g (1.0 mole) of 3-picoline was added. The mixture was transferred from the flask to a liter Magne Drive autoclave, using 100 cc of xylene to rinse the flask.

The autoclave was purged of air with nitrogen, pressurized to 30 pounds per square inch gauge (psig) with ammonia and to 600 psig with nitrogen. It was then heated rapidly with stirring to 145° C. and maintained at 145°–152° C. for 12 hours. The pressure reached 1040 psig during the heating period. At the end of the heating, the autoclave was cooled to room temperature and vented to atmospheric pressure. The reaction mixture was carefully hydrolyzed with 150 cc of water. The xylene layer was separated and the aqueous phase was extracted again with 25 cc of xylene. Both xylene extracts were combined and distilled to give 72.4 g of distillate with a freezing point of 60.6° C. A GLC analysis showed a ratio of 3.92:1 of 2-amino-5-methylpyridine to 2-amino-3-methylpyridine in the isomer products. This ratio differed substantially from the corresponding about 1:10.5 ratio of these isomers reported by Abramovitch and other literature references. The recovered 2-amino-5-methylpyridine was useful in the synthesis of various herbicides. It also has uses in pharmaceutical and insecticidal applications, and is reported in Gadekar, U.S. Pat. No. 3,974,281 (1976) to be used in the sythesis of Pirfenidone which is an analgesic, antipyretic, antiinflammatory compound and which is effective in treating a number of respiratory ailments.

EXAMPLE 2

Amination of 3-Picoline

A liter Magne Drive was equipped with a water cooled reflux condenser. Non-condensable gas was led from the reflux condenser through a pressure relief valve (set at 350 psig) to a vent. A mixture of 58.5 g (1.5 mole) of sodamide, 400 cc of xylene, 0.1 cc of oleic acid, 93 g (1 mole) of 3-picoline and 5.4 g (0.05 mole) of a mixture of 2-amino-5-methylpyridine and 2-amino-3-methylpyridine in a ratio of 2.9:1 was placed in the Magne Drive. The autoclave was purged of air with nitrogen and pressurized to 30 psig with ammonia and to 220 psig with nitrogen. Cooling water was turned on the reflux condenser. The autoclave was slowly heated to 152° C. at which time hydrogen evolution began. During this time the total pressure of the system reached 350 psig causing the pressure relief valve to activate. The reaction continued for about 5 hours, during which time the reaction temperature was gradually lowered to 140° C. without any noticeable drop in the reaction rate. When hydrogen evolution became very slow the autoclave was cooled to room temperature and vented to atmospheric pressure. The reaction mixture was carefully hydrolyzed with 150 cc of water. The xylene phase was separated and the aqueous phase was extracted again with 25 cc of xylene. Both xylene extracts were combined and distilled to give 84.7 g of distillate with a freezing point of 60.8° C. A GLC analysis showed a ratio of 2-amino-5-methylpyridine to 2-amino-3-methylpyridine of 3.69:1. This once again significantly improved upon prior reported ratios, and uses for the 2,5-isomer product were the same as in Example 1.

EXAMPLE 3

Amination of Nicotinic Acid

Into a liter Magne Drive, equipped as described in Example 2, was placed a slurry of 50.7 g (1.3 moles) of sodamide in 500 cc of xylene containing 0.1 cc of oleic acid. To the slurry was slowly added 73.9 (0.6 mole) of nicotinic acid. The acid formed the sodium salt with evolution of ammonia. The autoclave was closed and purged with nitrogen and pressurized to 30 psig with gaseous ammonia and then to 200 psig with nitrogen. The pressure relief valve was set at 355 psig. The Magne Drive was heated with stirring to 150° and kept within 150°-155° for 3.5 hours while hydrogen was released through the pressure relief valve. At the end of this heating period, hydrogen evolution ceased. The autoclave was continually heated for an additional 4 hours gradually increasing the temperature to a maximum of 200° C. There was very little gas evolved during this time. The autoclave was cooled to room temperature and vented to atmospheric pressure. The reaction mixture was carefully hydrolyzed with 150 cc of water. The aqueous layer was separated and the pH was adjusted to 6.0 with concentrated hydrochloric acid. At this pH a precipitate was obtained. It was filtered, washed with water and dried to give 21.3 g of 6-aminonicotinic acid, m.p. 315° C. with decomposition. The yield was 25.7%. The structure was verified by NMR and IR spectra. A mixed melting point with an authentic sample of 6-aminonicotinic acid gave no depression. This result differed substantially from literature reports such as Bojarska-Dahlig and Nantka-Namirski, *Roczniki Chem.*, 30, 621 (1956) which report that the result of the Chichibabin amination of nicotinic acid was the di-substituted 2,6-diaminopyridine. Applicants' 6-aminonicotinic acid product was useful in the preparation of pharmaceuticals for antacids and ulcer inhibitors, such as those disclosed in Regnier et al., Ger Offen. No. 2,419,535 (1974).

EXAMPLE 4

Amination of Nicotinamide

A mixture of 50.7 g (1.3 moles) of sodamide preformed in situ as in Example 1, 400 cc of xylene containing 0.1 cc of oleic acid and 73.3 g (0.6 mole) of nicotinamide was placed in an autoclave such as the one described in Example 2. The autoclave was closed and purged of air with ammonia. It was pressurized to 60 psig with ammonia and 200 psig with nitrogen. The pressure relief valve was set at 360 psig. The autoclave was heated to 122°-145° C. and maintained within this temperature range for 3 hours during which time hydrogen was evolved. The reaction mixture was cooled to room temperature and carefully hydrolyzed with 150 cc of water. Maximum temperature during hydrolysis was 18° C. The hydrolyzed mixture was filtered. The filter cake was washed with water and dried to give 14.3 g of 6-aminonicotinamide, m.p. 240°-247° C. The aqueous phase of the filtrate was separated and adjusted to pH 6.0 with concentrated hydrochloric acid. A precipitate formed which was filtered, washed with water and dried to give 5.4 g of 6-aminonicotinic acid, m.p. 314° C. with decomposition. The yield of 6-aminonicotinamide was 17.4% and the yield of 6-aminonicotinic acid was 6.5%. Both structures were confirmed by IR and NMR spectra. This result significantly differed from prior art references which report the classic Chichibabin amination product of nicotinamide to be exclusively 2-aminonicotinamide. Caldwell, Tyson and Lauer, *J. Am. Chem. Soc.*, 66, 1479 (1944). Uses for the 6-aminonicotinic acid product of applicants' reaction were the same as stated in Example 4, whereas the recovered 6-aminonicotinamide was found effective as a rodenticide as reported in Johnson, Can. Pat. No. 1,089,763, for its inhibitory effect against Lactobacillus arabinosus as reported in Kitamura, et al., *Yakugaku Zasshi*, 95, 547 (1975).

EXAMPLE 5

Amination of 3-Hydroxypyridine

A mixture of 89.7 g (2.3 moles) of sodamide, 500 cc of xylene containing 0.1 cc of oleic acid and 95 g (1 mole) of 3-hydroxypyridine was placed in a Magne Drive as described in Example 2. The autoclave was closed and purged of air with ammonia, pressurized with ammonia to 40 psig and to 200 psig with nitrogen. The pressure relief valve was set at 350 psig. The mixture was heated (158°-186°) for almost 5 hours, during which time hydrogen was evolved. The autoclave was cooled to room temperature, vented to atmospheric pressure and hydrolyzed with 250 cc of water. The temperature during the hydrolysis was 60° C. The aqueous phase was separated and neutralized to pH 7.0 with concentrated hydrochloric acid. It was extracted 3 times with 4-picoline. The picoline extracts were combined and distilled to give 39.3 g of recovered 3-hydroxypyridine and 40.6 g of 2-amino-3-hydroxypyridine boiling 223°-228° C. at 29 mm. The melting point of the 2-amino-3-hydroxypyridine, recrystallized from methanol-xylene, was 162°-163° C. The structure was confirmed by NMR and the IR spectrum was identical to the spectrum of 2-amino-3-hydroxypyridine found in *Aldrich Library of Infrared Spectra*, 2nd ed., p. 1157E. The yield of 2-amino-3-hydroxypyridine, based on 3-hydroxypyridine recovered, was 62.9%. This result significantly differed from the literature report by Levitt and Levitt, *Chemistry and Industry*, 1621 (1963) which reports the amination of 3-hydroxypyridine gave 2,6-diaminopyridine in good yield while also pointing out that 2-amino-3-hydroxypyridine should, in fact, not be obtained. This is not true of applicants' discovery. The recovered 2-amino-3-hydroxypyridine was found useful, for example, in preparing prostaglandin synthetase inhibitors as reported in Belg. Patent 830,786 (1975), in preparing antiinflammatory agents, analgesics and antipyretics as reported in Shen, et al., Ger. Offen. 2,330,109 (1974), and in preparing antibacterials as reported in Meszaros et al., *Hung Teljes*, 10,957 (1975). The 2-amino-3-hydroxypyridine was also found useful in the preparation of metalized azo dyes for dying wool, polyamide, and acrylic fibers as reported in Back and Buehler, Ger. Offen. Nos. 2,236,299 (1973) and 2,236,269 (1973).

EXAMPLE 6

Amination of 4-Dimethylaminopyridine

A mixture of 54.6 g (1.4 moles) of sodamide preformed in situ as in Example 1, 400 cc of xylene containing 0.1 cc of oleic acid, 9.4 g (0.1 mole) of 2-aminopyridine and 122 g (1 mole) of 4-dimethylaminopyridine was placed in a Magne Drive such as the one described in Example 2. The autoclave was closed and purged of air with ammonia, pressurized to 50 psig with ammonia and to 200 psig with nitrogen. The pressure relief value was set at 360 psig. The mixture was heated at 145°–160° C. for 6.5 hours. Hydrogen was evolved during this time. The autoclave was cooled to room temperature, vented to atmospheric pressure and hydrolyzed with 150 cc of water. A mass of crystals were observed in the autoclave. The mixture was heated to about 75° C. and 100 cc of 4-picoline was added to dissolve the solids. The addition of the picoline caused 3 phases to form, a top xylene phase, a middle picoline phase which contained some xylene and most of the reaction product, and a bottom aqueous caustic phase. The phases were separated at about 70° C. The aqueous phase was extracted again with 4-picoline. The picoline extracts were combined and treated with dry ice to neutralize any caustic. The extracts were distilled until dry and the residue was filtered hot (to remove inorganic salts). To the filtrate was added toluene and the solution was allowed to cool. Crystals formed on cooling. They were filtered at room temperature, washed with toluene and dried to give 64.9 g of 4-aminopyridine, m.p. 156°–162° C. The yield was 69%. The filtrate could have been distilled to yield more 4-aminopyridine. This result differed significantly from a prior report by Pozharskii, et al., *Khim. Geterotsikl. Soedin.*, 1232 (1973) that a standard Chichibabin amination of 4-(dimethylamino)pyridine gave a yield of 30% of 2-amino-4-(dimethylamino)-pyridine. Applicants' recovered 4-aminopyridine product was found to have many uses as reported in the literature, including use in the protection of corn fields from blackbirds as reported in DeGrazio, et al., *J. Wildl. Manage.*, 36, 1316 (1972) and Stickley, et al., *J. Wildl. Manage.*, 40, 126 (1976), and as hardening accelerators for epoxy resins as reported by Nishimura, *Japan. Kokai*, No. 74 48,800 (1974).

EXAMPLE 7

Amination of 4-(5-Nonyl)pyridine

A mixture of 50.7 g (1.3 moles) of sodamide preformed in situ as in Example 1, 350 cc of xylene containing 0.1 cc of oleic acid, and 205 g (1 mole) of 4-(5-nonyl)pyridine was placed in a Magne Drive such as the one described in Example 2. The autoclave was closed and purged of air with nitrogen, pressurized to 10 psig with ammonia and 200 psig with nitrogen. The pressure relief valve was set at 350 psig. The mixture was heated to 173° C. at which temperature amination began. The temperature was reduced and the reaction was run at 158°–163° C. for 8.7 hours. Hydrogen was evolved during this time. The autoclave was cooled to room temperature, vented to atmospheric pressure and hydrolyzed with 150 cc of water. The xylene phase was separated and the bottom aqueous caustic phase was re-extracted with 25 cc of xylene. Both xylene extracts were combined and distilled to give 2-amino-4-(5-nonyl)pyridine boiling at 197°–225° C. at 22 mm Hg. The yield was 67.3%. This result substantially increases the yield of 2-amino-4-(5-nonyl)pyridine over that reported previously by one of the applicants, McGill, U.S. Pat. No. 4,177,349 (1979) and McGill, U.S. Pat. No. 4,267,335 (1981). In this prior work, 4-(5-nonyl)pyridine was shown to prefer to couple in the presence of sodamide, giving high yields of 4,4'-di-(5-nonyl)-2,2'-bipyridyl but only low yields of 2-amino-4-(5-nonyl)pyridine. This increased yield of 2-amino-4-(5-nonyl)pyridine is of importance because the compound has valuable biocidal properties.

EXAMPLE 8

Amination of 3,4-Lutidine

A mixture of 46.8 g (1.2 moles) of sodamide, 450 cc of toluene, 107 g (1 mole) of 3,4-lutidine and 5.0 g (0.05 mole) of 3-aminopyridine was placed in the apparatus described in Example 2. The autoclave was secured and purged of air with ammonia and pressurized to 45 psi with ammonia and then to 215 psi with nitrogen. The pressure relief valve was set at 365 psi. Cooling water was turned on the reflux condenser. The autoclave was heated with stirring to 185° C. at which temperature hydrogen evolution began. The reaction continued at 185°–189° C. for about 4 hours until hydrogen stopped coming through the pressure relief valve. The autoclave was cooled to room temperature and vented to atmospheric pressure. The reaction mixture was carefully hydrolyzed with 150 cc of water. The toluene phase was separated and the aqueous phase was extracted twice with 25 cc of toluene. All of the toluene extracts were combined and distilled to recover 22.9 g of 3,4-lutidine and 79.1 g of a mixture of 2-amino-3,4-dimethylpyridine and 2-amino-4,5-dimethylpyridine. The yield of both isomers based on 3,4-lutidine recovered was 81.1%. The ratio of 2-amino-3,4-dimethylpyridine to 2-amino-4,5-dimethylpyridine was 1.09:1. This ratio of almost equal isomers differed substantially from that in the literature which showed that the ratio of 2-amino-3,4-dimethylpyridine to 2-amino-4,5-dimethylpyridine of 3.5:1 was obtained from a Chichibabin reaction of 3,4-lutidine at atmospheric pressure in N,N-dimethylaniline. Siegel, *J. Heterocyclic Chem.*, 18, 1613 (1981). The isomer 2-amino-4,5-dimethylpyridine is useful in preparing 1,3-bis(2'-pyridylimino)isoindoline chelating ligands.

EXAMPLE 9

Amination of 3-(3-Phenylpropyl)pyridine

There was placed in a liter Magne Drive, equipped as described in Example 2, a mixture of 46.8 g (1.2 moles) of sodamide, 450 cc of toluene containing 0.1 cc of oleic acid, 5.0 g (0.05 mole) of 4-aminopyridine, and 197 g (1.0 mole) of 3-(3-phenylpropyl)pyridine. The autoclave was closed and purged with ammonia and pressurized to 45 psi with ammonia and then to 215 psi with nitrogen. The pressure relief valve was set at 365 psi. Cooling water was turned on the reflux condenser. The autoclave was slowly heated with stirring to 168° C. at which temperature moderate hydrogen evolution began. The reaction continued to evolve hydrogen for 3.5 hours to a maximum temperature of 186° C. The autoclave was cooled and vented to atmospheric pressure. The reaction mixture was hydrolyzed with 150 cc of water (maximum temperature was 50° C.). The toluene phase was separated and the aqueous phase was extracted twice with 50 cc of toluene. The toluene extracts were combined, treated with carbon dioxide to neutralize any caustic present, and distilled to recover 23.9 g of 3-(3-phenylpropyl)pyridine and 150.4 g of a mixture of 2-amino-5-(3-phenylpropyl)pyridine and 2-amino-3-(3-phenylpropyl)pyridine boiling at 182°–198° C. at 2 mm Hg. A GLC analysis of the mixture showed a ratio of 2,5-isomer:2,3-isomer of 5.9:1. The yield of both isomers, based on 3-(3-phenylpropyl)pyridine recovered, was 80.7%. This ratio differed greatly from the ratio obtained when 3-(3-phenylpropyl)pyridine was aminated with sodamide in refluxing xylene at atmospheric pressure. Under atmospheric pressure the ratio was turned around giving a 3.1:1 ratio 2,3-isomer:2,5-isomer. These two isomers, 2-amino-5-(3-phenylpropyl)pyridine and 2-amino-3-(3-phenylpropyl)pyridine are new compositions of matter. The 2,3- and 2,5-isomers are valuable for their biocidal properties.

EXAMPLE 10

Amination of 3-Phenylpyridine

A mixture of 33.2 g (0.85 mole) of sodamide, 450 cc of toluene containing 0.1 cc of oleic acid, and 126.9 g (0.82 mole) of 3-phenylpyridine was placed in a liter Magne Drive, equipped as described in Example 2. The autoclave was closed and purged of air with ammonia, pressurized to 45 psi with ammonia and then to 215 psi with nitrogen. Cooling water was turned on the reflux condenser. The autoclave was heated with stirring to 150° C. and maintained between 150° and 160° C. for about 3 hours, during which time hydrogen evolved and passed through the pressure relief valve. The autoclave was cooled to room temperature and vented to atmospheric pressure. The reaction mixture was carefully hydrolyzed with 100 cc of water. The toluene phase was separated and the aqueous phase was extracted twice with 25 cc of toluene. The toluene extracts were combined and distilled to give 46.9 g of a mixture of 2-amino-5-phenylpyridine and 2-amino-3-phenylpyridine boiling 201°–227° C. at 24 mm Hg. A GLC analysis showed that the ratio of 2,5-isomer:2,3-isomer was 38.1:1. The 2-amino-5-phenylpyridine, crystallized from pyridine, had a melting point of 136°–137° C. This ratio differed considerably from the ratio obtained when 3-phenylpyridine was aminated with sodamide in xylene at atmospheric pressure. The ratio obtained under atmospheric conditions was 11.0:1, 2,5-isomer:2,3-isomer. The 2-amino-5-phenylpyridine isomer was found to have useful biocidal properties.

EXAMPLE 11

Amination of 2-Aminopyridine

A mixture of 85.8 g (2.2 moles) of sodamide and 500 cc of toluene containing 0.5 cc of oleic acid was placed in a liter Magne Drive, equipped as described in Example 2. To the mixture was added 94 g (1.0 mole) of 2-aminopyridine. When the 2-aminopyridine came in contact with the sodamide, the sodium salt of 2-aminopyridine was formed with the evolution of ammonia. The ammonia evolution purged the autoclave of air. The vessel was closed and pressurized to 15 psi with ammonia and to 100 psig with nitrogen. The pressure relief valve was set at 100 psig. Cooling water was turned on the reflux condenser. The autoclave was heated to 180° C. with stirring. The temperature was maintained between 180°–185° C. for 2 hours while hydrogen was evolved and bled off through the pressure relief valve. The autoclave was cooled and carefully hydrolyzed at 50° C. with 100 cc of isopropanol and 150 cc of water. The organic phase was separated at about 50° C. The aqueous phase was re-extracted twice with a solution of 3 parts of toluene and 1 part of isopropanol. The extracts were combined and distilled to give 58.7 g of recovered 2-aminopyridine and 36.4 g of 2,6-diaminopyridine yield, based on 2-aminopyridine consumed, 88.8%. The 2,6-diaminopyridine is useful in the preparation of phenazopyridine, an antiseptic drug used in genitourinary tract infections.

EXAMPLE 12

Amination of 3-Ethylpyridine

A mixture of 46.8 g (1.2 moles) of sodamide, 400 cc of toluene containing 0.1 cc of oleic acid, and 107 g (1.0 mole) of 3-ethylpyridine was placed in a liter Magne Drive autoclave, equipped as described in Example 2. The vessel was purged of air with ammonia, pressurized to 30 psig with ammonia and then to 200 psig with nitrogen. The pressure relief valve was set at 350 psig. Cooling water was turned on the reflux condenser. The autoclave was slowly heated with stirring. The temperature reached 180° C. before hydrogen evolution began. After the amination started, the reaction continued for 3.5 hours while the temperature was gradually lowered to 151° C. The autoclave was cooled, vented to atmospheric pressure and carefully hydrolyzed with 150 cc of water. The toluene phase was separated and the aqueous phase was extracted again with 25 cc of toluene. Both toluene extracts are combined and distilled to give 90.9 g boiling 163° C. at 43 mm to 195° C. at 34 mm of a mixture of 2-amino-5-ethylpyridine and 2-amino-3-ethylpyridine. Yield of both isomers was 74.5%. An analysis of the mixture showed a ratio of 4.55:1 of 2-amino-5-ethylpyridine to 2-amino-3-ethylpyridine. The ratio is significantly different from the literature where it is reported 3.5:1, 2,3-isomer:2,5-isomer. Ban and Wakamatsu, *Chem. Ind.* 710 (1964). Uses for 2-amino-5-ethylpyridine were included in Example 1 in addition to its biocidal properties.

EXAMPLE 13

Amination of 3-n-Butylpyridine

A mixture of 46.8 g (1.2 moles) of sodamide, 400 cc of toluene containing 0.1 cc of oleic acid, and 135 g (1.0 mole) of 3-n-butylpyridine was placed in a liter Magne Drive autoclave, equipped as described in Example 2. The vessel was purged of air with ammonia, pressurized to 30 psig with ammonia and then to 200 psig with nitrogen. The pressure relief valve was set at 340 psig. Cooling water was turned on the reflux condenser. The autoclave was heated with stirring to 208° C. when hydrogen evolution began. Hydrogen continued to evolve for 2 hours. During the first hour, the autoclave was slowly cooled to 165° C. and then kept at 160°–165° C. for about another hour. The vessel was cooled, vented to atmospheric pressure and carefully hydrolyzed with 150 cc of water. The toluene phase was separated. The aqueous phase was extracted twice with 30 cc of toluene. The toluene phases were combined and distilled to recover 8.3 g of unreacted 3-n-butylpyridine and 114.7 g of a mixture of 2-amino-5-n-butylpyridine and 2-amino-3-n-butylpyridine, the mixture of two products boiling at 176°–194° C. at 76 mm. An analysis by GLC showed the ratio of the 2,5-isomer to the 2,3- isomer was 3.5:1. The yield of both isomers based on recovered 3-n-butylpyridine was 81.5%. The ratio obtained is greatly different from that reported in the literature where the ratio of 2,5-isomer to 2,3-isomer is stated as 1:4. Hardegger and Nikles, *Helv. Chim. Acta*, 39, 505 (1956). The 2-amino-5-n-butylpyridine is useful in the preparation of fusaric acid, a drug with hypotensive activity. Fusaric acid is also a Dopamine beta-hydroxylase inhibitor.

EXAMPLE 14

Amination of Pyridine

Into a liter Magne Drive, equipped as described in Example 2, were placed 93.6 g (2.4 moles) of sodamide, 450 cc toluene containing 0.1 cc of oleic acid, and 158 g (2 moles) of pyridine. The autoclave was purged of air with ammonia, pressurized to 15 psi with ammonia and then to 100 psig with nitrogen. The pressure relief valve was set at 100 psig. Cooling water was turned on the reflux condenser. The amination was run, with stirring, over 2.25 hours within a temperature range of 140°–165° C., during which time hydrogen was evolved through the pressure relief valve. The autoclave was cooled and vented to atmospheric pressure and carefully hydrolyzed with 250 cc of water. The toluene phase was separated and the aqueous phase was extracted again with 50 cc of toluene. Both toluene extracts were combined and distilled to obtain 148.3 g of of 2-aminopyridine and 7.4 g of 2,6-diaminopyridine. The yield of 2-aminopyridine, was 78.9% and the yield of 2,6-diaminopyridine was 6.8%. The 2-aminopyridine is useful as a starting material for antihistamines and the 2-6 diaminopyridine has the same use as given in Example 11.

What is claimed is:

1. In a Chichibabin amination of a pyridine base by sodamide in an organic solvent, the improvement comprising the steps of:
   (a) conducting the reaction under pressure of at least about 50 psi in the gas phase above the reaction mixture; and
   (b) adding ammonia to the mixture sufficient to produce a partial pressure of ammonia of at least about 5 psi in the gas phase.

2. The Chichibabin amination of claim 1 in which said adding is prior to said conducting.

3. The Chichibabin amination of claim 2 comprising the additional steps of:
   (a) placing the gas phase above the mixture under pressure of at least about 100 psi prior to said conducting; and
   (b) maintaining the gas phase under pressure of at least about 300 psi with at least some partial pressure of ammonia being present during said conducting.

4. The Chichibabin amination of claim 3 in which said placing said maintaining include using the autogenous evolution of gases from the mixture to pressurize the gas phase.

5. The Chichibabin amination of claim 3 in which said adding is in addition to any autogenous pressure of ammonia generated in situ from the reaction mixture.

6. The Chichibabin amination of claim 3 in which said adding includes the step of preparing the sodamide in situ in excess liquid ammonia prior to said conducting.

7. The Chichibabin amination of claim 3 in which said adding includes the step of injecting gaseous ammonia into the reaction vessel.

8. The Chichibabin amination of claim 7 in which said placing and said maintaining and said conducting are in a substantially inert atmosphere, and said adding is sufficient to produce a partial pressure of ammonia of at least about 15–50 psi in the gas phase prior to said conducting.

9. The Chichibabin amination of claim 8 in which said conducting is at a temperature between about 130°–200° C.

10. The Chichibabin amination of claim 9 in which the pyridine base is selected from the group consisting of:
    3-picoline;
    nicotinic acid;
    nicotinamide;
    3-hydroxypyridine;
    4-dimethylaminopyridine;
    4-(5-nonyl)pyridine;
    3-ethylpyridine;
    3-propylpyridine;
    3-isopropylpyridine;
    3-butylpyridine;
    3-(3-phenylpropyl)pyridine;
    3-phenylpyridine; and
    3,4-lutidine.

11. The Chichibabin amination of claim 9 in which the pyridine base is selected from the group consisting of:
    pyridine;
    2-aminopyridine;
    3-picoline;
    nicotinic acid;
    nicotinamide;
    3-hydroxypyridine;
    4-dimethylaminopyridine;
    4-(5-nonyl)pyridine;
    3-ethylpyridine;
    3-propylpyridine;
    3-isopropylpyridine;
    3-butylpyridine;
    3-(3-phenylpropyl)pyridine;
    3-phenylpyridine; and
    3,4-lutidine.

12. The Chichibabin amination of claim 9 in which said conducting is in the presence of a catalytic amount of an aminopyridine.

13. The Chichibabin amination of claim 9 in which said conducting is in the presence of a catalytic amount of a desired product of the reaction.

14. In a Chichibabin amination of a pyridine base by sodamide in an organic solvent, the improvement comprising the steps of:
    increasing pressure and adding ammonia in the gas phase above the reaction mixture sufficient to increase yield by at least about one third of a product expected in the Chichibabin amination or to produce a yield of at least about 10% of a product not expected in the Chichibabin amination, each yield being as a percent of total amination products obtained.

15. The Chichibabin amination of claim 14 in which said increasing is to a pressure of at least about 50 psi and said adding is to a partial pressure of ammonia of at least about 5 psi.

16. The Chichibabin amination of claim 15 comprising the additional step of conducting the reaction in a substantially inert atmosphere.

17. The Chichabibin amination of claim 16 in which said adding includes the step of preparing the sodamide in situ in excess liquid ammonia prior to said conducting.

18. The Chichibabin amination of claim 16 in which said adding includes the step of injecting gaseous ammonia into the reaction vessel.

19. The Chichibabin amination of claim 18 in which said conducting is in the presence of a catalytic amount of an aminopyridine.

20. The Chichibabin amination of claim 18 in which said conducting is in the presence of a catalytic amount of a desired product of the reaction.

21. The Chichibabin amination of claim 18 in which said increasing is to a pressure of at least about 200 psi and said adding is to a partial pressure of ammonia of at least about 15-50 psi.

22. The Chichibabin amination of claim 21 comprising the additional step of conducting the reaction at a temperature between about 130°-200° C.

23. The Chichibabin amination of claim 22 in which the pyridine base is selected from the group consisting of:
- 3-picoline;
- nicotinic acid;
- nicotinamide;
- 3-hydroxypyridine;
- 4-dimethylaminopyridine;
- 4-(5-nonyl)pyridine;
- 3-ethylpyridine;
- 3-propylpyridine;
- 3-isopropylpyridine;
- 3-butylpyridine;
- 3-(3-phenylpropyl)pyridine;
- 3-phenylpyridine; and
- 3,4-lutidine.

24. The Chichibabin amination of claim 23 in which said increasing is to a pressure of about 300 psi and said adding is to a partial pressure of ammonia of about 45 psi.

25. An improved Chichibabin amination, comprising the steps of:
(a) combining an amount of pyridine base and at least a slight stoichiometric excess of sodamide in an organic solvent in a closed reaction vessel;
(b) adding ammonia to the vessel to produce an initial partial pressure of ammonia of at least about 5 psi in the gas phase;
(c) placing the gas phase in the vessel under pressure of at least about 50 psi with a partial pressure of ammonia being at least equal to the autogenous pressure of ammonia generated in situ from the mixture;
(d) bringing the resulting mixture to a temperature sufficient to cause amination to begin; and
(e) maintaining the mixture at a temperature and for a period sufficient to cause substantial amination to occur.

26. The Chichibabin amination of claim 25 in which said maintaining further includes maintaining the gas phase in the vessel under pressure of at least about 100 psi with at least some partial pressure of ammonia being present during amination.

27. The Chichibabin amination of claim 26 comprising the additional step of using the autogenous pressure of gases evolved in situ during amination to accomplish said maintaining.

28. The Chichibabin amination of claim 27 in which said adding is prior to said bringing and said maintaining.

29. The Chichibabin amination of claim 28 in which said adding includes the step of preparing the sodamide in situ in excess liquid ammonia in the vessel prior to said combining.

30. The Chichibabin amination of claim 28 in which said placing and said maintaining under pressure and said adding of ammonia are sufficient to increase yield by at least about one third of a product expected in the Chichibabin amination or to produce a yield of at least about 10% of a product not expected in the Chichibabin amination, each yield being as a percent of total amination products obtained.

31. The Chichibabin amination of claim 28 in which said placing and said maintaining are under a substantially inert atmosphere.

32. The Chichibabin amination of claim 31 in which said placing is prior to said bringing.

33. The Chichibabin amination of claim 32 in which said adding is to at least about 15-50 psi of ammonia.

34. The Chichibabin amination of claim 33 in which said maintaining is to at least about 300 psi.

35. The Chichibabin amination of claim 34 in which said bringing is to a temperature at which hydrogen gas is evolved, and said maintaining is until hydrogen evolution has substantially ceased.

36. The Chichibabin amination of claim 35 in which said bringing and said maintaining are to a temperature between about 130°-200° C.

37. The Chichibabin amination of claim 36 in which said combining is in the presence of a catalytic amount of an aminopyridine.

38. The Chichibabin amination of claim 36 in which said combining is in the presence of a catalytic amount of a desired product of the reaction.

39. The Chichibabin amination of claim 36 in which said maintaining is without refluxing of the reaction mixture.

40. The Chichibabin amination of claim 36 comprising the additional step of venting off excess pressure from gases evolved during said maintaining.

41. The Chichibabin amination of claim 40 in which said adding includes the step of injecting gaseous ammonia into the reaction vessel.

42. The Chichibabin amination of claim 41 in which said combining is of a pyridine base selected from the group consisting of:
- 3-picoline;
- nicotinic acid;
- nicotinamide;
- 3-hydroxypyridine;
- 4-dimethylaminopyridine;
- 4-(5-nonyl)pyridine;
- 3-ethylpyridine;
- 3-propylpyridine;
- 3-isopropylpyridine;
- 3-butylpyridine;
- 3-(3-phenylpropyl)pyridine;
- 3-phenylpyridine; and
- 3,4-lutidine.

43. The Chichibabin amination of claim 41 in which the pyridine base is selected from said group consisting of:
- pyridine;

2-aminopyridine;
3-picoline;
nicotinic acid;
nicotinamide;
3-hydroxypyridine;
4-dimethylaminopyridine;
4-(5-nonyl)pyridine;
3-ethylpyridine;
3-propylpyridine;
3-isopropylpyridine;
3-butylpyridine;
3-(3-phenylpropyl)pyridine;
3-phenylpyridine; and
3,4-lutidine.

44. The Chichibabin amination of claim 40 comprising the additional step of purging the vessel of air prior to said placing.

45. The Chichibabin amination of claim 44 comprising the additional steps of:
   (a) cooling the reaction mixture and venting the vessel to atmospheric pressure after said maintaining; and
   (b) recovering the desired reaction product.

46. The Chichibabin amination of claim 45 in which the pyridine base is 3-picoline.

47. A new composition of matter, comprising 2-amino-5-(3-phenylpropyl)pyridine or 2-amino-3-(3-phenylpropyl)pyridine.

* * * * *